United States Patent
Torrens-Jover et al.

(10) Patent No.: US 6,187,930 B1
(45) Date of Patent: Feb. 13, 2001

(54) RESOLUTION OF AMINES

(75) Inventors: Antoni Torrens-Jover; Jordi Frigola-Constansa, both of Barcelona (ES)

(73) Assignee: Laboratorios Del Dr. Esteve, S.A., Barcelona (ES)

( * ) Notice: Under 35 U.S.C. 154(b), the term of this patent shall be extended for 0 days.

(21) Appl. No.: 09/462,326

(22) PCT Filed: Jul. 6, 1998

(86) PCT No.: PCT/ES98/00195

§ 371 Date: Apr. 10, 2000

§ 102(e) Date: Apr. 10, 2000

(87) PCT Pub. No.: WO99/02500

PCT Pub. Date: Jan. 21, 1999

(30) Foreign Application Priority Data

Jul. 10, 1997 (ES) .................................................... 9701538

(51) Int. Cl.$^7$ ................................................. C07D 231/12
(52) U.S. Cl. .......................................................... 548/375.1
(58) Field of Search ........................................... 548/375.1

(56) References Cited

FOREIGN PATENT DOCUMENTS

| 0787715 | 8/1997 | (EP) . |
| 9720817 | 6/1997 | (WO) . |

OTHER PUBLICATIONS

Jacques, J., et al., "Enantiomers, Racemates and Resolutions", *Krieger Publishing Company* pp 259–261, 387–388 (1991).

Hueso–Rodriguez, J.A., et al., "Preparation of the enantiomers of the analgesic E–3710" *Bioorganic & Medicinal Chemistry Letters*, vol. 3. No. 2, pp 269–272 (1993).

*Primary Examiner*—Robert W. Ramsuer
(74) *Attorney, Agent, or Firm*—Ladas & Parry

(57) ABSTRACT

The procedure comprises reacting the mixture that comprises 2-[phenyl(1-methyl-1 H-pyrazole-5-yl)methoxy]-N, N-dimethylethanamine (I) with an enantiomer of an optically active acid to form a diastereoisomeric salt, separating said salt and liberating the enantiomer of said compound (I). The dextrorotatory enantiomer of (I) can be obtained by reacting a racemic mixture or non-racemic mixture of (I) with (+)-ditoluyl-L-tartaric acid, optionally mixed with p-toluensulphonic acid. Compound (I) has analgesic properties and its most active enantiomer is dextrorotatory.

16 Claims, No Drawings

RESOLUTION OF AMINES

This application is a 371 of PCT/ES98/00195 filed Jul. 6, 1998.

FIELD OF THE INVENTION

This invention relates to a new procedure for the optical resolution of a mixture that comprises 2-[phenyl(1-methyl-1 H-pyrazole-5-yl) methoxy]-N,N-dimethylethanamine into its enantiomers.

BACKGROUND OF THE INVENTION

The compound 2-[phenyl(1-methyl-1 H-pyrazole-5-yl) methoxy]-N,N-dimethylethanamine (which can also be given the name 5-[α-(2-dimethylaminoethoxy)benzyl]-1-methyl-1 H-pyrazole or 5-{[N,N-dimethylaminoethoxy) phenyl]methyl}-1-methyl-1 H-pyrazole), of formula I

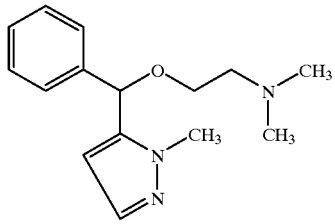

(I)

is a compound described in the European patent EP 289 380 which has analgesic properties.

The two enantiomers of the compound of formula I have been synthesised and their properties as analgesics evaluated [J. A. Hueso, J. Berrocal, B. Gutiérrez, A. J. Farré and J. Frigola, *Biorg. Med. Chem. Lett.* 1993, 3, 269]. It was found that the dextrorotatory enantiomer was the most active.

The enantiomers of the compound of formula I are obtained by O-alkylation of the corresponding enantiomers of [phenyl-hydroxy-(1-methyl-1 H-pyrazole-5-yl]methane, of formula II

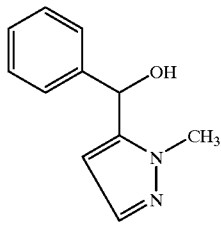

(II)

The dextrorotatory enantiomer of the compound of formula (II), hereinafter (+) -II, has been obtained from the synthesis of enantiomerically pure compounds (EPC) with very poor yield. The starting compound is (−)-ethyl madelate allowing an absolute configuration (R) to be assigned to the enantiomer (+)-II.

The enantiomers of the compound of formula (II) have also been obtained from laborious processes of separation of the diastereoisomeric esters formed by the reaction of (+)-II with (+)-O-acetylmandelic acid by column chromatography or by fractionated crystallisation. The yields obtained were 25% for the enantiomer (+)-II and 22% for the levorotatory enantiomer of the compound of formula (II), hereinafter (−)-II [J. A: Hueso, J. Berrocal, B. Gutiérrez, A. J. Farré and J. Frigola, *Bioorg. Med. Chem. Lett.* 1993, 3, 269].

The methods for resolving racemic mixtures are very abundant and have been extensively described [for a monograph on the properties of racemates and their resolution see: Jacques, Collet, Wilen, "Enantiomers Racemates and Resolutions", Wiley: New York, 1981; for reviews see: Wilen, *Top. Stereochem.*, 1971, 6, 107; Boyle, *Q. Rev. Chem. Soc.*, 1971, 25; Buss, Vermeulen, *Industrial. Eng. Chem.*, 1968, 60, 12 ].

A pair of the enantiomers can be resolved by different methods. The most commonly employed is that of separation thereof by fractionated crystallisation. If the racemic compound contains an amine group in its structure it is possible to form diastereoisomeric salts with an optically active acid. Tartaric acid and its derivatives, such as dibenzoyltartaric, ditoluyltartaric, o-nitrotartaric acid and others, malic acids, mandelic acid and its derivatives, 2-phenoxypropionic acid, quinic acid and canphorsulphonic acid and its derivatives, among others, are the most commonly used. Once the diastereoisomeric salts are obtained and separated, the enantiomeric amines can be easily liberated and the chiral acid recovered. This simple and economical method has been widely utilised on industrial scales.

The object of the present invention consists of providing a commercially useful procedure suitable for obtaining the two enantiomers of the compound of formula I separately with a high yield and suitable enantiomeric purity.

DETAILED DESCRIPTION OF THE INVENTION

The invention provides a procedure for resolving a mixture that comprises 2-(phenyl(1-methyl-1 H-pyrazole-5-yl) methoxy)-N,N-dimethylethanamine (I) into its dextrorotatory, hereinafter (+)-I, and levorotatory, hereinafter (−)-I, enantiomers. The absolute configuration of the enantiomer (+)-I is (R), while that of the enantiomer (−)-I is (S).

The procedure object of this invention comprises the steps of formation of a diastereoisomeric salt of an enantiomer of the compound of formula (I) with an enantiomer of an optically active acid, the separation of said diastereoisomeric salt and the liberation of the enantiomer of the compound of formula (I).

The procedure is based on the optical resolution of an amine (compound of formula I) by means of the use of an optically active acid in which at least one of its enantiomers is capable of forming a diasteroeisomeric salt with one of the enantiomers of the compound of formula (I). In particular, the procedure of the invention comprises the formation of a diastereoisomeric salt between an enantiomer of the compound of formula (I) and an enantiomer of a chiral acid of general formula III,

R—COOH (III)

where
R represents a radical that contains, at least, one asymmetric centre.

Examples of acids of formula III are tartaric acid and its derivatives, dibenzoyltartaric, ditoluyltartaric acid and others, malic, mandelic acids and their derivatives, canphorsulphonic acid and its derivatives, among others. The acid of formula III can be used either alone or as a mixture with other acids (adjuvant acids) that can be organic or inorganic, such as hydrochloric acid, p-toluensulphonic acid or methanosulphonic acid, in molar proportions that vary between 0.5% and 50% (this molar percentage refers to the total of the mixture of the chiral acid of formula (III) and the adjuvant acid). Preferably, the chiral acid of formula III is chosen from (+)-ditoluyl-L-tartaric acid and (−)-ditoluyl-D-tartaric acid, either on their own or mixed, individually, with p-toluensulphonic acid.

The procedure is carried out in an appropriate solvent or a mixture of appropriate solvents. Appropriate solvents include water, acetone, acetonitrile, methanol, ethanol, isopropanol, tert-butanol, dichloromethane, chloroform, carbon tetrachloride, dimethylformamide, dimethylsulphoxide, ethyl acetate, toluene, xylene, pentane, hexane, heptane, petrol ether, ethyl ether, isopropyl ether, tetrahydrofurane, 1,4-dioxane, ethyleneglycol, 1,2-dimethoxyethane, and in general, any solvent susceptible to being used in a chemical process. Preferably, the solvent used is isopropanol.

The procedure can be carried out at temperatures lying between −20° C. and the reflux temperature of the reaction mixture.

Once the diastereoisomeric salt is formed it can by separated by conventional methods such as chromatography and fractionated crystallisation, among others.

The liberation of the enantiomer of the compound of formula I can be performed by, for example, neutralising the diastereoisomeric salt formed with an alkaline solution to separate the enantiomer of the compound of formula I and the enantiomer of the chiral acid of formula III used which, if it is so desired, can be recovered to use in other reaction cycles.

The resolution procedure object of the present invention can by used to resolve mixtures that comprise both enantiomers of the compound of formula I in any proportion. Therefore, this procedure is applicable both to performing the optical resolution of a racemic mixture of the compound of formula I (that is to say, that in which the two enantiomers are present in a 1:1 ratio) and for the optical resolution of non-racemic mixtures of the compound of formula I (in which one of the enantiomers is present in greater proportion), obtained by any physical or chemical method. The present separation method allow to obtain products with an enantiomeric purity over 99.5%.

Presented below, by way of example, is a method for obtaining the enantiomers of the compound of formula I and its corresponding citrates. These examples are shown only in order to illustrate the procedure object of the present invention and so should not be considered as limiting the scope of the invention.

EXAMPLE

Resolution of (±) 2-[phenyl(1-methyl-1 H-pyrazole-5-yl) methoxy]-N,N-dimethylethanamine [(±)-I]

(−)-ditoluyl-L-tartaric acid (12.85 g, 33.3 mmol) are added to a mixture of 17.25 g (66.6 mmol) of (±)-I in isopropanol (90 ml), heating gently until the solid dissolves. Next, p-toluensulphonic acid (33.3 mmol) is added and the diastereoisomeric salt is precipitated out of solution by the addition of diethyl ether (240 ml), to give 16.8 g of a white solid whose diastereoisomeric purity can be determined by NMR. This solid is treated with p-toluensulphonic acid (0.32 equivalents) and recrystallised in isopropanol (85 ml) to give 10.85 g of salt. A second recrystallisation in isopropanol (55 ml) with p-toluensulphonic acid (0.13 equivalents) leads to 8.76 g of ditoluyl-L-tartrate of (R)-(+) -2-(phenyl(1-methyl-1 H-pyrazole-5-yl) methoxy3-N,N-dimethylethanamine; m.p. 132–133° C.; ([α]$_D$=−77.1 (c=1.0 MeOH). Next the base is liberated by treating with NaOH at 10% and extracted with chloroform to yield an oil which dissolves in ethanol and which is treated with monohydrate citric acid, crystallising the corresponding citrate of (R)-(+)-I (5.42 g) with an enantiomeric purity of 95.2% as determined by HPLC.

The mother liquors from the process described above can be combined to perform a procedure analogous to that described previously but using (+) -ditoluyl-D-tartaric acid with a view to obtaining the levorotatory enantiomer of the compound of formula I [(−)-I], with remnants of the practically racemic product remaining in the mother liquors which can be submitted once again to the same procedure.

For the enantiometric separation (−)-I, the base of the mother liquors is liberated (13.7 g, 52.9 mmol) and an operation analogous to that described previously is performed but using a mixture of (+)-ditoluyl-D-tartaric acid (11.64 g, 30.15 mmol) and p-toluensulphonic acid (4.33 g, 27,75 mmol) in isopropanol (60 ml) and precipitating with diethyl ether yields 14.8 g of the diastereoisomeric salt which is recrystallised four times in isopropanol to give 8.7 g of (S)- 2-[phenyl(1-methyl-1 H-pyrazole-5-yl) methoxy]-N,N-dimethylethanamine ditoluyl-D-tartrate; m.p. 134–136° C.; [α]$_D$=+77.0 (c=1.0 MeOH). Next the base is liberated and citrate is formed, which is recrystallised in ethanol to give 5.3 g of (S)-(−)-I citrate, with an enantiomeric purity of 98.9% as determined by HPLC; m.p. 128–129° C.; [α]$_D$=−12.0 (c=1.0 MeOH).

Next, another cycle is undertaken from 10.1 g of base, liberated from the mother liquors, (−) -ditoluyl-L-tartaric acid and p-toluensulphonic acid to obtain, after four recrystallisation steps and formation of (R)-(+)-I, 4.15 g of the final desired product with an enantiomeric purity of 98.5%, as determined by HPLC; m.p. 128–129° C.; [α]$_D$=+12.2 (c=1.0 MeOH).

The above description indicates, by way of example, a certain manner in which to proceed. In the case that enantiomers with a greater enantiomeric purity are desired one or more recrystallisations can be performed depending on the degree of purity that is required.

What is claimed is:

1. A process for resolving 2-[phenyl(1-methyl-1 H-pyrazole-5-yl)methoxy]-N,N-dimethylethanamine of formula I (I)

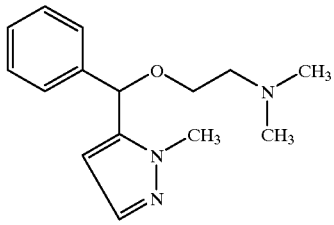

into its enantiomers comprising the steps of:
a) reacting 2-[phenyl(1-methyl-1 H-pyrazole-5-yl) methoxy]-N,N-dimethylethanamine with an optically active acid selected from (+)-ditoluyl-L-tartaric acid, (−)-ditoluyl-L-tartaric acid or a mixture thereof in a solvent to form a diastereoisomeric salt between one of the enantiomers of formula (I) and one of (+)ditoluyl-L-tartaric acid or (−)ditoluyl-L-tartaric acid;
b) separating the diastereoisomeric salt and
c) isolating the enantiomer of 2-[phenyl(1-methyl-1-pyrazole-5-yl)methoxy]-N,N-dimethylethanamine.

2. The process according to claim 1 further comprising adding p-toluensulphonic acid to the mixture of step a).

3. The process of claim 1 wherein, the solvent is selected from water, acetone, acetonitrile, methanol, ethanol, isopropanol, tert-butanol, dichloromethan, chloroform, carbon tetrachloride, dimethylformamide, dimethylsulphoxide, ethyl acetate, toluene, xylene, pentane, hexane, heptane, petroleum ether, ethyl ether, isopropyl ether, tetrahydrofuran, 1,4-dioxane, ethyleneglycol, 1,2-dimethoxyethane or mixtures thereof.

4. The process according to claim 1 wherein, step a) is earned out at a temperature between −20° C. and the reflux temperature of the reaction mixture.

5. The process according to claim 1 wherein, in step b) the diasteroisomeric salt is separated by fractionated crystallization or chromatography.

6. The process according to claim 1, wherein, separated diasterisomeric salt is neutralized by an alkaline solution to isolate the enantiomer of compound (I).

7. The process according to claim 1 wherein, the mixture that comprises compound (I) is a racemic mixture.

8. The process according to claim 1 wherein, the mixture that comprises compound (I) is a non-racemic mixture.

9. The process according to claim 1 wherein, the enantiomer obtained is (R)-(+)-2[phenyl(1-methyl-1 H-pyrazole-5-yl)methoxy]-N,N-dimethylethanamine.

10. The process according to claim 9 wherein, the optically active acid is (+)-ditoluyl-L-tartaric acid.

11. The process according to claim 9 wherein, (+)-ditoluyl-L-tartaric acid is used as a mixture with p-toluensulphonic acid.

12. The process according to claim 9 wherein, the solvent is isopropanol.

13. The process according to claim 1 wherein the enantiomer obtained is (S)-(−)-2-[phenyl(1-methyl-1 H-pyrazole-5-yl)methoxy]-N,N-dimethylethanamine.

14. The according to claim 13 wherein the optically active acid is (−)-ditoluyl-D-tartaric acid.

15. The process according to claim 13 wherein (−)-ditoluyl-D-tartaric acid is used as a mixture with p-toluensulphonic acid.

16. The process according to claim 13 wherein the solvent is isopropanol.

* * * * *